(12) United States Patent
Pell et al.

(10) Patent No.: US 11,364,225 B2
(45) Date of Patent: Jun. 21, 2022

(54) PHARMACEUTICAL FORMULATION FOR TREATING SYMPTOMS OF MIGRAINE AND CLUSTER HEADACHES, AND METHOD OF USING THE SAME

(71) Applicant: BN INTELLECTUAL PROPERTIES, INC., St. Petersburg, FL (US)

(72) Inventors: Donald M. Pell, St. Petersburg, FL (US); Paula Pell, St. Petersburg, FL (US); Michael Spuza, St. Petersburg, FL (US); Govindan Nair, Seminole, FL (US)

(73) Assignee: BN INTELLECTUAL PROPERTIES, INC., St. Petersburg, FL (US)

( * ) Notice: Subject to any disclaimer, the term of this patent is extended or adjusted under 35 U.S.C. 154(b) by 0 days.

(21) Appl. No.: 16/854,426

(22) Filed: Apr. 21, 2020

(65) Prior Publication Data

US 2021/0052552 A1    Feb. 25, 2021

Related U.S. Application Data

(63) Continuation-in-part of application No. 16/836,485, filed on Mar. 31, 2020, now abandoned, and a
(Continued)

(51) Int. Cl.
  *A61K 31/4045*  (2006.01)
  *A61M 11/00*  (2006.01)
  (Continued)

(52) U.S. Cl.
  CPC ........ *A61K 31/4045* (2013.01); *A61K 9/0078* (2013.01); *A61M 11/005* (2013.01);
  (Continued)

(58) Field of Classification Search
  CPC ........ A61H 11/001–003; A61H 11/005; A61K 9/0078; A61K 31/4045; A61P 25/06
  See application file for complete search history.

(56) References Cited

U.S. PATENT DOCUMENTS

| | | | |
|---|---|---|---|
| 5,554,639 A | * | 9/1996 | Craig ..................... A61P 25/06 514/415 |
| 6,805,854 B2 | | 10/2004 | Hale et al. |

(Continued)

FOREIGN PATENT DOCUMENTS

| | | |
|---|---|---|
| CA | 2650412 | 10/2007 |
| CN | 103285474 A | 9/2013 |

(Continued)

OTHER PUBLICATIONS

Cady et al., R.K., "Randomized, double-blind, crossover study comparing DFN-11 injection (3 mg subcutaneous sumatriptan) with 6 mg subcutaneous sumatriptan for the treatment of rapidly-escalating attacks of episodic migraine," The Journal of Headache and Pain, (2017) 18:17, pp. 1-8.

(Continued)

*Primary Examiner* — Valerie L Woodward
(74) *Attorney, Agent, or Firm* — Hauptman Ham, LLP

(57) ABSTRACT

A treatment for symptoms of migraine and cluster headaches includes operations of providing a solution of a serotonin receptor agonist (SRA) in an active mesh nebulizer, triggering the formation of a plume of particles from the active mesh nebulizer, and delivery of the plume of particles into the lungs of a patient during an inhalation process.

14 Claims, 1 Drawing Sheet

Related U.S. Application Data continuation-in-part of application No. 16/547,072, filed on Aug. 21, 2019, now Pat. No. 11,135,379.

(51) Int. Cl.
| | |
|---|---|
| *A61K 9/00* | (2006.01) |
| *A61P 25/06* | (2006.01) |
| *A61M 15/00* | (2006.01) |
| *A61B 5/00* | (2006.01) |

(52) U.S. Cl.
CPC ......... *A61M 15/0085* (2013.01); *A61P 25/06* (2018.01); *A61B 5/4824* (2013.01)

(56) References Cited

U.S. PATENT DOCUMENTS

| | | | | |
|---|---|---|---|---|
| 7,109,161 | B1* | 9/2006 | Gayed | A61K 9/0014 |
| | | | | 514/2.4 |
| 7,189,753 | B1* | 3/2007 | Cady | A61K 31/335 |
| | | | | 514/415 |
| 8,022,095 | B2 | 9/2011 | Plachetka | |
| 2003/0004127 | A1* | 1/2003 | Bountra | A61K 31/70 |
| | | | | 514/46 |
| 2003/0018031 | A1* | 1/2003 | Gutterman | A61K 2300/00 |
| | | | | 514/248 |
| 2006/0002989 | A1 | 1/2006 | Ahmed et al. | |
| 2006/0276510 | A1* | 12/2006 | Abu-Shakra | A61K 31/4412 |
| | | | | 514/332 |
| 2007/0088006 | A1* | 4/2007 | Cady | A61K 31/16 |
| | | | | 514/165 |
| 2007/0166336 | A1 | 7/2007 | Delmarre et al. | |
| 2012/0071510 | A1 | 3/2012 | Leone-Bay et al. | |
| 2012/0322736 | A1* | 12/2012 | Yeomans | A61P 25/06 |
| | | | | 514/11.6 |
| 2014/0010866 | A1* | 1/2014 | Fossel | A61K 31/437 |
| | | | | 424/450 |
| 2014/0239525 | A1* | 8/2014 | McConville | A61P 21/02 |
| | | | | 264/5 |
| 2015/0104506 | A1 | 4/2015 | Hansen et al. | |
| 2015/0144129 | A1 | 5/2015 | Djupesland et al. | |
| 2016/0129182 | A1* | 5/2016 | Schuster | G16H 40/63 |
| | | | | 702/56 |
| 2016/0199453 | A1* | 7/2016 | Hoffman | A61K 8/361 |
| | | | | 424/667 |
| 2016/0303361 | A1* | 10/2016 | Sameti | A61K 31/4468 |
| 2017/0119040 | A1* | 5/2017 | Cameron | A24F 47/008 |

FOREIGN PATENT DOCUMENTS

| | | |
|---|---|---|
| EP | 1527773 A1 | 5/2005 |
| WO | 2012064892 A1 | 5/2012 |
| WO | 2017023361 A1 | 2/2017 |

OTHER PUBLICATIONS

Derry et al., C.J., "Sumatriptan (oral route of administration) for acute migraine attacks in adults (Review)," Cochrane Library, Cochrane Database of Systematic Reviews, 2012, Issue 2, pp. 1-258.

Derry et al., C.J., "Sumatriptan (oral route of administration) for acute migraine attacks in adults—overview of Cochrane reviews (Review)," Cochrane Library, Cochrane Database of Systematic Reviews, 2012, Issue 2, pp. 1-48.

Obaidi et al., M., "Improved Pharmacokinetics of Sumatriptan With Breath Powered™ Nasal Delivery of Sumatriptan Powder," Research Submission, Headache, 2013, pp. 1-11.

Tfelt-Hansen, P.C., "Does sumatriptan cross the blood-brain barrier in animals and man?," J. Headache Pain, (2010) 11:5-12, pp. 1-8.

Sumatriptan, en.wikipedia.org/wiki/Sumatriptan, pp. 1-8.

International Search Report and Written Opinion issued in corresponding International Application No. PCT/US2020/029799, dated Jul. 9, 2020, pp. 1-16, U.S. Patent and Trademark Office, Alexandria, VA.

* cited by examiner

100

102 Determine a patient dose of serotonin receptor agonist for a patient.

104 Determine a dose delivery profile for the patient dose.

106 Provide a solution with serotonin receptor agonist.

108 Generate a plume of particles of the solution of serotonin receptor agonist using an active mesh nebulizer.

110 Direct the plume of particles into patient lungs.

112 Evaluate patient condition.

114 Determine whether to provide an additional plume of particles to the patient.

PHARMACEUTICAL FORMULATION FOR TREATING SYMPTOMS OF MIGRAINE AND CLUSTER HEADACHES, AND METHOD OF USING THE SAME

CROSS REFERENCE AND PRIORITY CLAIM

This application is a continuation of, and claims priority to, U.S. patent application Ser. No. 16/547,072, titled "METHOD OF DELIVERING PHARMACEUTICAL PRODUCTS" and filed on Aug. 21, 2019, which is incorporated herein by reference in its entirety. Further, the related U.S. patent application Ser. No. 16/836,485, titled "NEBULIZER FOR TIME-REGULATED DELIVERY" and filed on Mar. 31, 2020, is incorporated herein by reference in its entirety.

BACKGROUND

Abortive treatments to stop symptoms of migraine and cluster headaches are directed to reduction of the severity of headache symptoms. Sub-lingual and oral treatments for migraine and cluster headaches are frequently associated with nausea and other side effects which limit their use in persons having cardiovascular disease and compromised renal and hepatic performance. Treatment using sub-cutaneous injection of medications is associated with reduced nausea symptoms.

Migraine headache symptom patterns have sufficient lead time before headache onset to prepare for abortive treatments to reduce symptoms before or during the main headache.

Cluster headache symptom patterns occur with a rapidity which makes abortive treatments more difficult because the natural symptom pattern often abates before the abortive treatment has had time to fully take effect.

BRIEF DESCRIPTION OF THE DRAWINGS

FIG. 1 is a flow diagram of a method of treating symptoms of a migraine headache or cluster headaches in a patient, in accordance with some embodiments.

DETAILED DESCRIPTION

The following disclosure provides many different embodiments, or examples, for implementing different features of the provided subject matter. Specific examples of components, values, operations, materials, arrangements, etc., are described below to simplify the present disclosure. These are, of course, merely examples and are not intended to be limiting. Other components, values, operations, materials, arrangements, etc., are contemplated. The present disclosure may repeat reference numerals and/or letters in the various examples. This repetition is for the purpose of simplicity and clarity and does not in itself dictate a relationship between the various embodiments and/or configurations discussed. Although the operations of the method disclosed herein are presented in one order, other orders of the operations of the method disclosed herein are also within the scope of the present disclosure.

The present disclosure relates to delivery of a medical product containing a serotonin receptor agonist (SRA) by means of an inhaled plume of particles generated by an active mesh nebulizer to alleviate symptoms of migraine and cluster headaches. A receptor agonist is a compound which binds to and activates a receptor in a tissue. Receptor agonists trigger physiological responses after receptor activation. Symptoms of migraine and cluster headaches are alleviated more quickly by inhalation of a SRA in a plume of particles generated by a nebulizer according to one or more embodiments than the other methods described below. In at least one embodiment, the nebulizer is an active mesh nebulizer as described in U.S. patent application Ser. No. 16/836,485, incorporated herein by reference. According to theory and belief, serotonin receptor agonists relieve symptoms of migraine and cluster headaches by [1] triggering vasoconstriction of cerebral vascular tissue, and [2] triggering an anti-inflammatory response in cerebral tissue, reducing the overall swelling within the cranium associated with migraine and cluster headache symptoms. In some embodiments, the anti-inflammatory response reduces already-present inflammation. In some embodiments, the anti-inflammatory response stops an inflammatory response from proceeding, but does not reverse already-present inflammation.

A migraine headache is a headache in which persistent throbbing pain occurs, most frequently, on just one side of the head. Migraine headaches occur in approximately 10% of the population. The strength of migraine headache symptoms is highly variable between individuals. Symptoms of migraine headaches include nausea, vomiting, and sensory sensitivity to light, sounds, or smells. In some instances of migraine headache, a person experiences an aura, or visual disturbance prior to the onset of the above-mentioned symptoms. In some instances, an aura occurs without onset of migraine headache. In some instances of a migraine headache, a person experiences an aura during the above-mentioned symptoms. Once begun, migraine headache symptoms last for between several hours and up to three days in an individual. Migraine headache symptoms occur with a frequency of several times per year, to several times per week according to individual presentations of symptoms in patients.

A cluster headache is a disorder which includes recurrent severe headaches on one side of the head (often around the eye or near the temple). Cluster headaches are described as having more pronounced pain than even migraine headaches. Individual cluster headaches last between about 15 minutes and several hours. Cluster headache recurrence is difficult to predict. In some instances, individual attacks and cluster grouping occur at regular intervals, and in some instances individual attacks occur with apparently random frequency. Cluster headache recurrence is described as episodic, with multiple attacks occurring on a daily basis for several weeks, followed by long headache-free periods (remission), or as chronic, with multiple headaches occurring on a daily basis for months or years with no remission.

Migraine headaches and cluster headaches result in direct costs to a person seeking treatment and opportunity costs associated with treatment and recovery time, including lost work time and reduced work effectiveness for many persons. Improved effectiveness of treatments for migraine headaches and cluster headaches is expected to result in lowered direct costs to persons seeking relief, and reduced opportunity costs for patients and employers by increasing worker availability and effectiveness. Improved effectiveness of treatment for migraine headaches and cluster headaches involves decreasing the time between treatment and symptom relief, increasing the amount of relief provided to a patient by treatment, and increasing the amount of time between bouts of symptoms experienced by the patient after treatment.

Symptoms associated with migraine and cluster headaches are believed to arise from elevated pressure within the skull or cranium. Elevated intra-cranial pressure is believed to trigger nociceptors in the head and other parts of the body to produce the pain, nausea, and visual disturbances associated with migraine and cluster headaches. Treatment using medications such as non-steroidal anti-inflammatory drugs (NSAIDs, e.g., acetaminophen, ibuprofen, naproxen sodium, aspirin, and so forth) that reduce inflammation are sometimes effective at reducing symptoms of migraine and cluster headaches. As described above, a serotonin receptor agonist delivered to a patient is believed to relieve symptoms of migraine and cluster headaches for some patients by [1] causing the blood vessels in the brain to constrict, relieving some of the intra-cranial pressure, and [2] blocking and/or reducing cranial inflammation. Reducing intra-cranial pressure and blocking inflammatory response reduces signals in reduction of symptom severity, Some methods of using an SRA to treat migraine and cluster headache symptoms include sub-lingual delivery, oral delivery, intra-nasal delivery, and sub-cutaneous delivery. One aspect of sub-lingual delivery, oral delivery, intra-nasal delivery, and sub-cutaneous delivery of SRAs is that relief is delayed because the absorption of the SRAs into the bloodstream, or delivery of the absorbed SRAs to the brain, is relatively slow.

The present disclosure relates to delivery of an SRA by means of an inhaled plume of particles generated by an active mesh nebulizer. Symptoms of migraine and cluster headaches are alleviated more quickly by inhalation of an SRA in a plume of particles generated by an active mesh nebulizer than the other methods described above.

FIG. 1 is a flow diagram of a method 100 of treating symptoms of a migraine headache or cluster headaches in a patient, in accordance with some embodiments. A person of ordinary skill will understand that the order in which the operations of method 100 are performed are varied according to different embodiments in order to provide symptom relief to patients, without restricting the scope of the present disclosure.

SRAs suitable for treatment of symptoms of migraine headaches and cluster headaches include, among others, vasoconstrictors which modify calcium uptake of smooth muscle in vascular tissue. According to theory and belief, serotonin receptor agonists which act on 5-hydroxytryptamine (5-HT) receptors and vascular smooth muscle tissue promote elevation of blood pressure and decrease of intra-cranial pressure to alleviate symptoms of migraine headaches and cluster headaches. According to theory and belief, the 5-HT SRAs are fairly selective at causing vasoconstriction in cerebral vascular tissue by regulating calcium ion channels through membranes to promote vascular constriction. 5-HT receptors are divided into families, according to the receptor type and mechanism by which the receptor functions. 5-HT receptors located in blood vessels and the central nervous system and associated with vasoconstriction include the 5-$HT_{1A}$, 5-$HT_{1B}$, and 5-$HT_{1D}$ receptors, among other 5-HT receptor types. The 5-$HT_{1F}$ receptor is located in the central nervous system, rather than in vascular tissue, and is known to be associated with the regulation of migraine symptoms. According to theory and belief, activation of 5-$HT_1$-type receptors on sensory nerve endings prevents inflammation and alleviates the symptoms of migraine and cluster headaches.

Tryptamine-based drugs of the triptan family of SRAs are used in many migraine and cluster headache treatments. Triptans are SRAs which activate 5-$HT_{1B}$ and 5-$HT_{1D}$ receptors. Triptans have largely replaced ergotamines in treatment of migraine and cluster headaches in patients whose symptoms are not alleviated by non-steroidal anti-inflammatory drugs (NSAIDS) such as, e.g., ibuprophen, acetominophen, aspirin, and naproxen sodium. Triptans are delivered in sub-lingual (under the tongue) tablets, oral form (e.g., swallowed and absorbed through the stomach and intestines), nasal spray, suppositories, sub-cutaneous injection, and transdermal patches. Triptans used and/or considered for treatment of migraine and cluster headache symptoms include sumatriptan (Chemical Abstracts Service (CAS) number 103628-46-2), rizatriptan (CAS number 145202-66-0), naratriptan (CAS number 121679-13-8), eletriptan (CAS number 143322-58-1), donitriptan (CAS number 170912-52-4), almotriptan (CAS number 154323-57-6), frovatriptan (CAS number 158930-17-7), avitriptan (CAS number 151140-96-4), and the like. Side effects of using a SRA such as a triptan-type medication to treat symptoms of migraine and cluster headaches include coronary vasospasm, transient myocardial ischemia, myocardial infarction, ventricular tachycardia, and ventricular fibrillation. Excessive use of triptans or other SRAs can result in a patient experiencing serotonin syndrome. Patients having a history of cardiovascular disease, renal dysfunction, or uncontrolled hypotension are usually excluded from treatment using compounds of the triptan family of migraine medications because of the risk of serious complications and side effects described above.

Method 100 includes an optional operation 102, in which a patient dose of a SRA is determined for delivery to a patient. The patient dose of the SRA is determined according to, among other factors, patient age, patient pre-existing medical conditions, the patient body mass, the effectiveness of previous treatments of the patient with SRAs (e.g., individual sensitivity to medications), other medications which a patient is taking at the time of treatment, bioavailability of the SRA, and the like.

A patient dose of a SRA, for an active mesh nebulizer, is an amount of medication provided to a patient in a single session of using an active mesh nebulizer to treat symptoms of migraine or cluster headache. In some embodiments, a patient dose of the SRA delivered in the plume of particles is a uniform quantity provided to adult patients. In some embodiments of the method, a fixed-size patient dose is delivered repeatedly to a patient until relief of the symptoms of migraine and cluster headaches is achieved. In some embodiments, a single patient dose is determined on an individual basis according to a patient's medical history, sensitivity to the medication, and the severity of symptoms experienced on a historical basis, such that a single patient dose is enough to relieve the headache symptoms. According to some embodiments, a patient dose of SRA is determined by taking a patient dose of the SRA for sub-cutaneous treatment of symptoms, and dividing by a factor of 2. In some embodiments, the patient dose of a SRA for use in an active mesh nebulizer is determined by taking a patient dose of the SRA for oral or sub-lingual treatments and dividing by a factor ranging from not less than 2 to a factor not more than 12. In some embodiments, the patient dose of a SRA for use in an active mesh nebulizer treatment is determined by taking a patient dose of the SRA and dividing by a factor ranging from not less than 10 to not more than 20.

Bioavailability of a medication is a measure of the amount of medication accessible to the body in the vascular or circulatory system after delivery. According to theory and belief, the bioavailability of a SRA delivered by a plume of particles generated from an active mesh nebulizer is greater than the bioavailability of SRAs delivered by, e.g., sublingual delivery, oral delivery, nasal spray, and sub-cutaneous injection, because the droplets of SRA are absorbed directly through the alveoli into the bloodstream upon inhalation. As described above in optional operation 102 of method 100, the patient dose of SRA is determined prior to providing a solution of SRA (operation 106) for generating the plume of particles containing the SRA (operation 108). Bioavailability of SRA increases as the residence time of the SRA outside of the target tissue is decreased. For example, oral delivery of SRAs typically has the lowest bioavailability of the delivery paths described above because some medicine undergoes degradation in the stomach prior to absorption into the bloodstream, and some medicine undergoes degradation by metabolism in the liver (e.g., the first pass effect) prior to binding with the target tissues (e.g., the central nervous system or the vascular smooth muscle tissue 5-HT receptors). Sub-lingual delivery of SRA has a larger amount of bioavailability because the medication bypasses the gastrointestinal tract. According to theory and belief, delivery of an SRA by an active mesh nebulizer plume delivered to the lungs has a bioavailability nearly comparable to the bioavailability of intravenous delivery because of the high absorption rate, or uptake rate, through the lungs.

According to some embodiments, a patient dose of subcutaneous SRA comprises 6 milligrams (mg) of sumatriptan succinate delivered by an auto-injection device. In some embodiments, a patient dose of SRA comprises not more than 4 mg sumatriptan succinate delivered to a patient from a solution in an active mesh nebulizer. In some embodiments, a patient dose of sumatriptan (e.g., sumatriptan succinate in water) ranges from 0.3 to 3 mg of compound in a single treatment session, and repeated as needed until migraine or cluster headache symptoms are alleviated.

In some embodiments, the patient dose of SRA is from about 0.5 mg to about 10 mg rizatriptan (CAS number 145202-66-0) in water. In some embodiments, the patient dose of SRA is from about 0.1 mg to about 2.5 mg naratriptan (CAS number 121679-13-8). In some embodiments, the patient dose of SRA is from about 2 mg to about 40 mg eletriptan (CAS number 143322-58-1). In some embodiments, the patient dose of SRA is from about 0.3 mg to about 12.5 mg almotriptan (CAS number 154323-57-6). In some embodiments, the patient dose of SRA is from about 0.05 mg to about 2.5 mg frovatriptan (CAS number 158930-17-7). In some embodiments, the patient dose of SRA is from about 0.02 mg to about 2.5 mg zolnatriptan (CAS number 139264-17-8).

Method 100 includes an optional operation 104, in which a dose delivery profile for the patient dose is determined, in accordance with some embodiments. In some embodiments, a dose delivery profile is pre-programmed into the nebulizer and provides a fixed amount of medication to a patient based on standard dose sizes for patients receiving treatment for migraine and cluster headache symptoms. In some embodiments, the dose delivery profile of the SRA in the medication is fixed (such as in an embodiment where the patient dose has a fixed size) and the patient dose is delivered according to the fixed dose delivery profile repeatedly until the patient achieves symptom relief.

In some embodiments, the dose delivery profile is tailored to an individual patient such that following a single dose delivery profile delivers a full quantity of a tailored patient dose, and the full quantity of the tailored patient dose achieves symptom relief. In some embodiments, a dose delivery profile of a SRA is determined by evaluating the amount of SRA to be delivered to a patient and a concentration of SRA in a solution of the SRA, as well as the ability of a patient to perform an inhalation process to absorb the SRA through the lungs. As described in patent application (U.S. patent application Ser. No. 16/836,485, titled "NEBULIZER FOR TIME-REGULATED DELIVERY"), a dose delivery profile includes one or more periods of time (plume intervals) during which a plume of particles is generated from solution in a vial or capsule inserted into an active mesh nebulizer. In some embodiments, the plume interval ranges from 2-10 seconds, although other plume generation times are also possible. A dose delivery profile includes one or more plume intervals repeated with pauses in plume generation until the patient dose is delivered to the patient. In some embodiments, the dose delivery profile for the patient dose is determined by [1] calculating the amount of SRA delivered into a flow of air passing through the active mesh nebulizer for each second of operation of the active mesh to produce the plume of particles, [2] dividing the patient dose by the amount of SRA delivered per second of operation, and [3] dividing the dividend of [2] by a length of time that the active mesh operates for each inhalation of medication.

In a non-limiting example, a patient is prescribed a dose of 3 milligrams (mg) of a SRA (e.g., sumatriptan succinate). An active mesh nebulizer is provided to the patient, where the active mesh nebulizer contains a solution of sumatriptan succinate (20 mg/ml) and produces a plume of particles from the solution at a rate of 0.2 ml/minute. By multiplying the plume production rate (0.2 ml/min.) by the concentration of the solution (20 mg/ml), a delivery rate of 4 mg of solution per minute of plume production by the nebulizer. Dividing the prescribed dose (e.g., the patient dose) by the delivery rate, one is able to determine that the dose is able to be delivered with 40 seconds of plume production, as follows:

$$T = \left[\frac{D \times C}{k_n \times [M]}\right] \quad \text{Equation (1)}$$

where:
T is the plume production time, in seconds, to deliver a patient dose D,
C is a constant for converting between minutes and seconds,
$k_n$ is the nebulization rate, or the rate of plume production (mg/ml) and
[M] is the concentration of medication in the solution.
Thus, for [M]=20 mg/ml, C=60 sec/minute, $k_n$=0.2 ml/minute, and D=3 mg, T=45 seconds as provided in Equation (2):

$$T = \left[(3 \text{ mg})\left(\frac{60 \text{ sec.}}{1 \text{ min.}}\right)\left(\frac{1 \text{ min.}}{0.2 \text{ ml}}\right)\left(\frac{1 \text{ ml}}{20 \text{ mg}}\right)\right] = 45 \text{ seconds.} \quad \text{Equation (2)}$$

However, a patient is unable to inhale continuously for 45 seconds in order to receive the patient dose D. Thus, the plume production time T is divided into smaller plume production intervals ranging from about 5 to about 10 seconds in length, although other smaller intervals are also within the scope of the present disclosure, and a final delivery interval corresponds to the remainder of time, as follows. In a non-limiting example, the smaller interval is selected to be 8 seconds long, such that the 45 seconds of total plume production time is divided into 5 smaller intervals of 8 seconds each, and a final delivery interval of 5 seconds for delivering the patient dose of 3 mg. Other smaller intervals are also within the scope of the present disclosure in order to facilitate treatment of persons having different lung capacity, whether due to age, or medical history (emphysema, loss of lung tissue), and the like.

According to some embodiments, the medical product (e.g., the solution of SRA) is at a pH ranging from about 2 to about 7. The delivery of medical product having a low pH does not irritate the lung tissue because the small particle (or, droplet) size affords the particles a sufficiently long entrainment time during inhalation that the particles do not impact the lungs in the upper 3 branches, where irritation results in triggering of the cough reflex and expulsion of the inhaled particles of medical product.

The pH of the medical product ranges from about 2 to about 7 based on the solubility of the SRA in the medical product (e.g., in water) and the solubility modifications incurred by any additional compounds added to the medical product. In some embodiments, high-solubility inorganic salts promote dissolution (e.g., increase the solubility of SRAs). Many SRAs are delivered to a patient as organic salts formed by the reaction of a weak acid with a basic moiety (e.g., an amine group) of the medication molecule. Thus, the "salt effect" promotes solubility, (e.g., increases the solubility of the molecule, thus increasing the solubility product $K_{sp}$) and thus promotes biological activity the medication and boosts the speed with which the medication acts. Inorganic salts suitable for use as solubility enhancers of SRA-based medical products have a $K_{sp}$ ranging from about $1 \times 10^{-6}$ to about $1 \times 10^{-2}$, although other values of $K_{sp}$ are also within the scope of the present disclosure.

Method 100 includes an operation 106, in which a solution of the SRA is provided to a patient, in accordance with some embodiments. The SRA (e.g., the medication) is typically an aqueous solution of the SRA. In some embodiments, the SRA is in a pure or free-base form. In some embodiments, the SRA is a pharmaceutically acceptable excipient, or salt form of the pure active compound (e.g., the SRA). In some embodiments, the SRA delivered in a patient dose is a mixture of a salt form and a free-base form of the medication. Such salts include, e.g., without limitation, the following: hydrochloric acid, hydrobromic acid, acetic acid, maleic acid, formic acid, fumaric acid, and succinic acid salts. Pharmaceutically acceptable excipients may be volatile or nonvolatile.

In some embodiments, a small amount of an inorganic salt, such as sodium chloride, is added to promote solubility. In some embodiments, the medical product is an aqueous solution of an organic salt, such as sumatriptan succinate. In some embodiments, other inactive ingredients are also added to the medication in order to promote solubility, adjust or balance pH, and the like.

For example, in a non-limiting embodiment, the SRA comprises sumatriptan succinate dissolved in water. In a non-limiting embodiment, the SRA comprises sumatriptan succinate and sodium chloride in water. An amount of sumatriptan in the solution ranges from 0.3 mg/ml to about 3 mg/ml. The amount of inorganic salt (e.g., sodium chloride, potassium chloride, and the like) in the solution can range from 0 weight percent to 0.2 weight percent, in accordance with some embodiments. In some embodiments, the amount of sumatriptan in solution ranges from about 0.05 mg/ml to about 0.3 mg/ml. Solutions such as the aforementioned selected to treat symptoms of migraine and cluster headaches for patients with side effects and/or high sensitivity to medications, and so forth. In some embodiments, the amount of sumatriptan in solution ranges from about 0.3 mg/ml to about 1 mg/ml. In some embodiments, the amount of sumatriptan in solution ranges from about 1 mg/ml to about 3 mg/ml, although other formulations with higher sumatriptan concentrations are also envisioned within the scope of the present disclosure. Concentrations of sumatriptan in solution below the lower limit described above, although functional in terms of treatment, take longer to administer, reducing the likelihood that a patient will receive the full dose. Concentrations of sumatriptan in solution above the upper limit described above, although functional in terms of treatment, are associated with side effects in the patient including, e.g., serotonin syndrome and/or decreased liver and kidney function.

Method 100 includes an operation 108 in which a plume of particles of the solution of SRA is generated using an active mesh nebulizer. In some embodiments, the plume of particles of SRA is provided to a patient during the onset of migraine or cluster headache symptoms. In some embodiments, the plume of particles of SRA is provided to a patient after onset of migraine or cluster headache symptoms.

Migraine headache symptoms follow a pattern which spans hours or days before the onset of the headache. The phases of the migraine symptom pattern include: prodrome, aura, the actual headache, or the pain phase, and the postdrome, or the post-headache effects.

Prodrome symptoms occur in about 60% of migraine headaches between 2 hours and 2 days prior to the onset of the pain or aura. Aura symptoms occur in about one third of migraine headache symptom patterns and last from between several minutes to about one (1) hour. Visual symptoms of aura occur in about 98% of migraine headache patterns, and include flickering alterations of the visual field. In some embodiments, the aura occurs and the migraine symptom pattern terminates without proceeding to the headache or pain phase. The pain phase comprises a moderate to severe throbbing pain in the head. In most headaches, the pain is on one side of the head, but in about 40% of headaches, the pain is bilateral. The pain phase lasts from about 4 hours to about 72 hours in adults and is frequently accompanied by symptoms including: nausea, physical sensitivity (e.g., to light, sounds, and/or odors), fatigue, blurred vision, and vomiting. The postdrome includes soreness in the area of the migraine, impaired thinking, fatigue or feeling "hung over," and cognitive difficulty.

A pattern of symptoms for cluster headaches sometimes includes an aura, but the main headache usually occurs without the aura, and lasts for between 15 minutes and about 3 hours.

According to theory and belief, treatment of migraine and cluster headache symptoms with a plume of particles from an active mesh nebulizer, as described herein, relieves symptoms of cluster headache within about 10 minutes of treatment without the accompanying nausea from sub-lingual or oral treatments of, e.g., sumatriptan succinate, and without performing an injection as with subcutaneous treatment of sumatriptan succinate solutions.

As described in U.S. patent application Ser. No. 16/836, 485, titled "NEBULIZER FOR TIME-REGULATED DELIVERY," the active mesh nebulizer used for generating the plume of particles generates particles, at least 95% of the particles having individual particle diameters ranging from about 0.5 μm to about 5.0 μm. In some embodiments, at least 98% of the particles have individual particle diameters ranging from about 0.5 μm to about 5.0 μm. In some embodiments, at least 95% of the particles have individual particle diameters ranting from about 0.5 μm to about 3.0 μm. In some embodiments, at least 98% of the particles have individual particle diameters ranging from about 0.5 μm to about 3.0 µm. Particles larger than 5.0 µm have an increased likelihood of impacting the lung tissue prior to entering the alveoli, reducing the total amount of material delivered to the bloodstream. Particles of about 3 µm in diameter are more likely to be entrained into the alveoli because, according to theory and belief, despite water uptake during inhalation, the final particle diameter is still below about 5 µm. Particles that impact the lung tissue before entering the alveoli have a low absorption rate because the particles dissipate on the surface of the lung tissue, intermix with fluids and secretions on the lung tissue, and are swept out of the lungs by the cilia prior to absorption. According to theory and belief, particles within the above-specified range (e.g., about 0.5 µm to about 5.0 µm) are entrained with airflow moving into the alveoli and are absorbed through the alveoli into the bloodstream.

The particles can absorb water from the lung environment while passing through to the alveoli. Particles having smaller individual diameters are more likely to be reach the alveoli without impacting other lung tissue because such particles do not absorb enough water to grow larger than 5.0 µm. Particles having an individual diameter of about 5.0 µm are more likely to absorb water from the lung environment and become sufficiently large to impact the lung tissue before reaching the alveoli, or to be too large to enter the alveoli after entrainment deep into the lungs.

In some embodiments, the dose delivery profile of a SRA may include a single plume of particles generated by the active mesh nebulizer and inhaled by a patient. In some embodiments, the dose delivery profile of a SRA may include multiple plumes of particles generated by the active mesh nebulizer and inhaled by a patient, wherein the plumes of particles are intermixed with periods during which a patient exhales prior to a new inhalation or inspiratory period.

Method 100 includes an operation 110, in which a plume of particles is provided for a patient to inhale, in accordance with some embodiments. According to some embodiments, the patient begins an inhalation event (or an inspiratory event) before the active mesh nebulizer begins to generate a plume of particles as part of the dose delivery profile, and the active mesh nebulizer stops production of the plume of particles before the inhalation event ends. In some embodiments, multiple plumes of particles are generated for patient inhalation. A plume of particles is provided for inhalation by the patient by having the patient place a nebulizer mouthpiece or nozzle in the mouth prior to an inhalation, activating the nebulizer during an inhalation, and halting nebulizer operation prior to the end of the inhalation. In some embodiments, a flow of air enters the mouthpiece or nozzle of the nebulizer through holes in the sides of the mouthpiece or nozzle, the flow of air entraining the generated plume of particles during inhalation. According to theory and belief, the particles are carried into the alveoli and absorbed into the bloodstream during a single inhalation event. According to theory and belief, the particles are fully absorbed into the bloodstream and no particles are exhaled from the lungs.

Method 100 includes an operation 112, in which patient condition is evaluated after delivery of the patient dose of the SRA. In some embodiments, patient condition is evaluated by having a medical caregiver, or the patient herself, compare a present (e.g., after the delivery of the patient dose of the SRA) condition to the condition before delivery of the patient, dose, and determining a degree of change between the initial medical condition and a symptom-free condition. Method 100 further includes an operation 114, in which a determination is made whether to provide an additional plume of particles to the patient for a subsequent patient dose of the SRA. In some embodiments, the determination is made to provide the additional plume of particles (e.g., a second patient dose) under a continuing of the migraine or cluster headache symptoms. In some embodiments, the determination is made to withhold the additional plume of particles (e.g., the second patient dose) upon the migraine or cluster headache symptoms having ceased or reduced in intensity to the degree that a patient is able to function without pain or postdrome symptoms. A description of treatment of a patient which highlights the performance of operation 112 and operation 114 is provided below.

Non-Limiting Example of Treatment Protocol

A patient dose of SRA delivered to a patient by means of a plume of particles generated from an active mesh nebulizer as described above in operation 108 is expected to produce relief from symptoms (relief time) of migraine or cluster headaches within about 10 minutes from the delivery of the patient dose. In some embodiments, the relief from symptoms of migraine or cluster headaches is expected to occur within about 5 minutes from the delivery of the patient dose in the inhaled plume of particles.

Relief time from symptoms by an inhaled plume of particles is significantly faster than the relief time of migraine or cluster headaches from sub-lingual, oral, intranasal, or sub-cutaneous delivery of SRAs such as, e.g., sumatriptan succinate. Sub-lingual delivery of zolmitriptan achieves symptom relief within about 30 minutes, according to theory and belief. Sub-cutaneous delivery of sumatriptan succinate achieves patient relief (relief time) within about 60-90 minutes after injection. Oral delivery achieves patient relief within about 60 and 120 minutes. Intra-nasal delivery of sumatriptan succinate achieves patient relief within about 30-60 minutes, according to theory and belief.

In a non-limiting example, an adult female with a history of chronic migraine headaches was treated for migraine headache symptoms during the pain phase using an inhaled plume of particles from an active mesh nebulizer as described herein, and as described in U.S. patent application Ser. No. 16/836,485, titled "NEBULIZER FOR TIME-REGULATED DELIVERY". The female was provided with an active mesh nebulizer containing a solution of sumatriptan succinate in water at 0.1996 weight % (wt %) [e.g., 4 mg sumatriptan succinate in 2 grams of water, such that (0.004 g sumatriptan succinate/2.004 g solution)*100=0.1996 wt % sumatriptan succinate] which produced a plume of particles where over 95% of the particles have individual particle diameters ranging from about 0.5 µm to about 3.0 µm. The active mesh nebulizer was configured to produce a plume of particles by nebulizing the sumatriptan succinate solution at a rate of 0.2 milliliters per minute (ml/min) for one minute, resulting in a patient dose for a first inhalation session (e.g., six 10-second inhaled plume pulses) of not more than 4 mg sumatriptan succinate. According to theory and belief, a similar result (see below) is achieved with a smaller dose (e.g., not more than 3 mg of sumatriptan succinate) because the patient did not completely inhale the produced particles.

Upon completion of delivery of the patient dose in six ten-second inhalation/inspiratory periods, the patient waited 5 minutes and self-evaluated for migraine symptoms and reported that the migraine headache symptoms had completely abated.

The female had indicated in her medical history that she had regularly experienced migraine headache symptoms, at a frequency of about 3-4 episodes per week, over several months prior to the treatment. Subsequent to treatment of the female medical provider's migraine headache symptoms with the inhaled plume of sumatriptan succinate particles, she remained in remission for more than seven days.

According to theory and belief, the short time period until relief exhibited by the above-mentioned treatment of the female medical provided occurs by rapid absorption of the SRA in the plume of particles through the alveoli, into the blood stream, and the rapid delivery of SRA from the freshly oxygenated blood which leaves the lungs, passes through the left atrium and the left ventricle of the heart, through the aorta, and through the jugular, carotid arteries, and other arteries to the capillary/other vascular tissue in the brain. The surface area of the lung alveoli is extremely large, as is the interior surface area of the capillaries and small arteries of the brain. The surface area to volume ratio (or the circumference to cross-sectional area) of the arteries which flow to the brain, on the other hand, have an extremely low surface area (or circumference) to volume (or cross-sectional area) as compared to the alveolar tissue and brain capillaries. The relatively reduced surface area of the vessels which flow to the brain reduces the amount of diffusion of medications absorbed into the blood (in the alveoli) to the arterial walls and exterior tissues before reaching the brain tissue, where the high-surface area capillary/other vascular tissue promote rapid diffusion of the SRA from the bloodstream into the vascular tissue and the central nervous system. The smaller diameter of the capillaries and small cerebral arteries reduces the diffusion distance for the medications in the bloodstream to reach the vessel walls and nerve tissue beyond.

According to theory and belief, the rapid delivery of SRA from the alveoli to the brain vascular tissue and central nervous system (e.g., within about 10 seconds from delivery of the plume of particles to the lungs) produces a condition of receptor saturation in the brain and vascular tissue. Receptor saturation is a condition in which a large fraction, or perhaps all, of a receptor type in a type of tissue, are activated by the agonist or medication so delivered. The rapidity of delivery, the degree and the rate of receptor saturation are believed to combine to cause a synergistic effect in patients treated with the SRA, resulting in a relief time much shorter than the relief time of the other methods of headache symptoms described above.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of treating symptoms of migraine headache or cluster headache, comprising:
   providing a solution in an active mesh nebulizer, the solution having
      at least 99% by weight of water, and
      a serotonin receptor agonist (SRA);
   receiving, in a processor of the active mesh nebulizer, information regarding a prescribed dose of the SRA;
   calculating instructions for how to deliver the prescribed dose of the SRA based on a delivery rate of the SRA through an active mesh of the active mesh nebulizer, and the prescribed dose of the SRA;
   generating at least one plume of particles of the solution having the SRA using the active mesh nebulizer, wherein generating the plume of particles is based on the instructions provided by the processor of the active mesh nebulizer to vibrate the active mesh of the active mesh nebulizer;
   providing the at least one plume of particles to a patient during inhalation; and
   monitoring delivering the prescribed dose of the SRA by monitoring an amount of time that an active mesh of the active mesh nebulizer vibrates to produce the plume of particles.

2. The method of claim 1, further comprising
   evaluating patient headache symptoms subsequent to directing the plume of particles into the lungs of the patient; and
   determining whether to provide an additional prescribed dose of the SRA.

3. The method of claim 2, wherein evaluating patient headache symptoms comprises:
   waiting, subsequent to directing the plume of particles into a lung of the patient during inhalation, from 5 to 10 minutes.

4. The method of claim 3, further comprising:
   determining, based on a result of evaluating patient headache symptoms, whether to generate another plume of particles of the solution having the SRA; and
   generating a second plume of particles of the solution having the SRA; and
   directing the second plume of particles into the lungs of the patient during inhalation.

5. The method of claim 1, wherein the SRA is a solution of a 5-hydroxytryptamine (5-HT) agonist in water.

6. The method of claim 5, wherein providing a solution having a SRA in the active mesh nebulizer further comprises providing a solution of a $5\text{-HT}_{1B}$, a $5\text{-HT}_{1D}$, or a $5\text{-HT}_{1F}$ agonist in water.

7. The method of claim 6, wherein providing a solution having a $5\text{-HT}_{1B}$, a $5\text{-HT}_{1D}$, or a $5\text{-HT}_{1F}$ agonist further comprises providing a SRA in the triptan family in water.

8. The method of claim 7, wherein providing a SRA in the triptan family further comprises providing a solution containing sumatriptan succinate in water.

9. The method of claim 5, wherein providing the dose of SRA further comprises providing a solution of a $5\text{-HT}_{1B}$, a $5\text{-HT}_{1D}$, or a $5\text{-HT}_{1F}$ agonist in water.

10. The method of claim 1, wherein the SRA solution comprises a 5-hydroxytryptamine (5-HT) agonist in water.

11. A method of relieving symptoms of migraine or cluster headache, comprising:
   receiving, in a controller of the active mesh nebulizer, information regarding a prescribed dose of the SRA in an SRA solution;
   determining a number of vibration periods of an active mesh of the active mesh nebulizer to deliver the prescribed dose of the SRA, wherein the number of vibration periods is based on a delivery rate of the SRA through the active mesh of the active mesh nebulizer, and wherein the number of vibration periods corresponds to vibrating the active mesh for a first vibration time;
   generating at least one plume of particles of the SRA solution by vibrating the active mesh for each vibration period of the number of vibration periods;

providing the plume of particles of the SRA solution to a patient during at least one a first inhalation; and monitoring delivering the dose of the SRA by monitoring an amount of time that the active mesh of the active mesh nebulizer vibrates to produce the plume of particles.

12. The method of claim 11, further comprising:

evaluating patient headache symptoms following providing the patient the plume of particles during the first inhalation; and determining whether to provide an additional dose of the SRA to the patient.

13. The method of claim 12, wherein evaluating patient headache symptoms further comprises:

waiting, after providing the plume of particles of the SRA solution to a patient during the first inhalation, from 5 to 10 minutes before evaluating patient headache symptoms.

14. The method of claim 13, further comprising:

determining, based on a result of evaluating patient headache symptoms, whether to generate another plume of particles of the SRA solution;

generating a second plume of particles of the SRA solution; and providing the plume of particles of the SRA solution to a patient during a second inhalation.

* * * * *